(12) United States Patent
Fried et al.

(10) Patent No.: US 6,725,118 B1
(45) Date of Patent: Apr. 20, 2004

(54) METHOD OF PROVIDING CENTRALIZED SPLINT PRODUCTION

(76) Inventors: Scott Fried, P.O. Box 186, 209 Cathcart Rd., Gwynedd Valley, PA (US) 19437; Luke Michas, 58 Tum A Lum Cir., Westerly, RI (US) 02891; Jeremy Howard, 16 Austin La., Little Compton, RI (US) 02837

( * ) Notice: Subject to any disclaimer, the term of this patent is extended or adjusted under 35 U.S.C. 154(b) by 0 days.

(21) Appl. No.: 10/321,305

(22) Filed: Dec. 17, 2002

(51) Int. Cl.$^7$ .............................. G06F 19/00; A61F 5/00
(52) U.S. Cl. ............................................. 700/118; 602/5
(58) Field of Search ................................. 700/117, 118, 700/119, 120, 163, 98, 90, 95; 602/5, 6, 900, 4, 17–31

(56) References Cited

U.S. PATENT DOCUMENTS

| | | | | |
|---|---|---|---|---|
| 5,344,390 A | * | 9/1994 | Motloch | 602/23 |
| 5,365,996 A | * | 11/1994 | Crook | 164/45 |
| 5,372,572 A | * | 12/1994 | Tamagni | 602/16 |
| 5,539,649 A | * | 7/1996 | Walsh et al. | 700/163 |
| 6,402,713 B1 | * | 6/2002 | Doyle | 602/26 |
| 6,463,351 B1 | * | 10/2002 | Clynch | 700/163 |

* cited by examiner

*Primary Examiner*—Leo Picard
*Assistant Examiner*—Ryan Jarrett
(74) *Attorney, Agent, or Firm*—Volpe and Koenig, P.C.

(57) ABSTRACT

A method of providing centralized custom splint production for a network of healthcare providers. The method includes: providing a plurality of scanning devices located throughout the network; scanning a portion of a person's body for which a splint is needed to assemble at least one set of data representing an outer surface of the portion of the person's body, the scanning is performed using one of the plurality scanning devices; transmitting a signal representing the at least one set of data to a splint generating device; producing a custom splint contoured to complement the portion of the person's body.

26 Claims, 2 Drawing Sheets

METHOD OF PROVIDING CENTRALIZED SPLINT PRODUCTION

BACKGROUND

The present invention is generally directed to splints and, more specifically, to a method of providing custom splints. The custom splints can be used for any body part and can also be used to provide relief from carpal tunnel syndrome, tendinitis and other wrist and hand ailments.

In addition to the myriad of fractures experienced by people of all ages, millions of workers also find themselves experiencing hand and wrist pain on a frequent basis. Chronic pain can result in debilitating circumstances that drastically lower one's quality of life. Fractured bones, carpal tunnel syndrome and repetitive strain injury are some of the most common causes of chronic pain. Chronic pain can lead to depression, loss of livelihood, and scores of other secondary problems.

Allowing fractured bones to heal requires proper splinting of the body part. Custom splints are expensive and can be very time consuming to obtain. Additionally, health care networks don't have any centralized way of providing custom splints to patients.

In connection with carpal tunnel problems, most people still suffer, and have learned the hard way—after the physical toils and financial expense of surgery—that carpal tunnel is a problem with no easy surgical solution. Originally, carpal tunnel was mainly experienced by elderly people who had worked hard their entire lives, and then retired to lower activity levels. In the mid 1950's, Doctor George Phalen coined the term "carpal tunnel" to describe their condition, which was thought to be a localized nerve injury at the hand and wrist. The paradigm concerning upper extremity nerve injury taught in medical schools was "all nerve problems in the upper extremities are carpal tunnel." Since these patients had surgery and, because of sedentary lifestyles, died at a fairly young age, the incidence of returning pain symptoms was low and surgery appeared to be a suitable cure to carpal tunnel syndrome. Dr. Phalen did not envision that the straightforward problem he diagnosed and surgically treated would become as complex to treat as it has become today.

Today, carpal tunnel surgeries are often performed with minimal attempts being made to provide a complete pre-surgical diagnosis and to provide patient education to find non-surgical alternatives. Doctors rarely consider recommending activity and lifestyle modifications. Up to thirty percent of patients have recurrent or continued problems with pain and dysfunction after surgery, yet in spite of this, many feel they cannot improve because they have already had corrective surgery.

In the past, the belief that surgery is the best option was often unquestioned. Employers and insurance carriers wanted to believe that there is a quick fix to carpal tunnel and repetitive strain injury. Surgery was encouraged and patients were not told of the failure rates. Today, the recurrence of painful symptoms after undergoing carpal tunnel surgery is thought to be as high as thirty percent.

Many people who have had surgery continue to be symptomatic, but their complaints fall upon deaf ears. Most go back to their work activities and are warned not to complain anymore, or their jobs will be jeopardized. They are told the numbness, tingling and upper arm pain that they experience are to be expected and that "if you work hard, you are going to have some aches and pains."

The concepts of repetitive strain injury, tendinitis and carpal tunnel are misunderstood by many physicians and therapists. With the lack of knowledge and understanding of nerve injuries that permeates the medical community, patients are left to deal with the consequences—the return of their daily pain. They fall through the cracks of a system devastatingly deficient in understanding and treating these diseases.

One difficulty with finding non surgical methods to treat carpal tunnel syndrome is the need to immobilize the joint during periods of rest. While generic splints are available for immobilizing joints, such splints may result in the joint being held in a less than ideal alignment. The "cocked-up" wrist position resulting from most store bought splints fails to immobilize the wrist in a neutral position. By providing a custom splint tailored to the exact dimensions of a patient's hand, a time tested, side-effect free alternative to surgery can be used to obtain relief and healing. Custom splints also play an integral role when used with therapy and simple lifestyle modifications. One of the greatest benefits of a custom splint is that a custom splint can, in some cases, provide the needed relief to allow patients to consider non-surgical options. Unfortunately, few treatment centers have skilled personnel capable of making custom splints in a cost effective manner. Additionally, in most treatment centers, it is necessary for a patient to return for a second visit just to have the completed custom splint applied to the body.

It would be advantageous to provide a method of providing a custom splint that allowed a user to obtain a splint custom made for a portion of the user's body; that could preferably be manufactured by a remotely located splint generating machine; that can preferably provide multiple splints in a cost efficient manner; and that preferably allows the splint to be shipped to a user after it has been manufactured.

SUMMARY

Briefly stated, one embodiment of the present invention is directed to a method of providing centralized custom splint production for a network of healthcare providers. The method includes: providing a plurality of scanning devices located throughout the network; scanning a portion of a person's body for which a splint is needed to assemble at least one set of data representing an outer surface of the portion of the person's body, the scanning is performed using one of the plurality scanning devices; transmitting a signal representing the at least one set of data to a splint generating device; producing a custom splint contoured to complement the portion of the person's body.

In a separate embodiment, the present invention is directed to a method of making a custom splint for a portion of a person's body. The method includes: scanning a portion of the person's body for which a splint is needed to assemble at least one set of data representing an outer surface of the portion of the person's body; transmitting a signal representing at least one set of data to a splint generating device; and producing a custom splint contoured to complement the portion of the person's body.

BRIEF DESCRIPTION OF THE DRAWINGS

The above summary, as well as the following detailed description of the preferred embodiments of the present invention, will be understood when read in conjunction with the appended drawings. For the purpose of illustrating the invention, there are shown in the drawings embodiments which are presently preferred. It is understood, however, that the invention is not limited to the precise arrangement and instrumentalities shown. In the drawings.

DETAILED DESCRIPTION OF THE PREFERRED EMBODIMENTS

Certain terminology is used in the following description for convenience only and is not limiting. The word "outer" and/or "outwardly" refer to directions away from or to a location on an outer surface relative to the geometric center of the referenced element and designated parts thereof. The term "transmitted" is defined as including its normal meanings, as well as, including "the storing of data into a memory storage device by a first device so that the memory storage device is then transported to a second device that reads the data in the memory storage device such that the data is effectively transmitted from the first device to the second device via the memory storage device." The term "memory storage device" is defined to include "any one of a CD-ROM, diskette, DVD, removable hard drive, flash memory device, tape back-up or the like". Additionally, the words "a" and "one" are defined as including one or more of the referenced item unless specifically stated otherwise. The terminology includes the words above specifically mentioned, derivatives thereof, and words of similar import.

Figure 1:
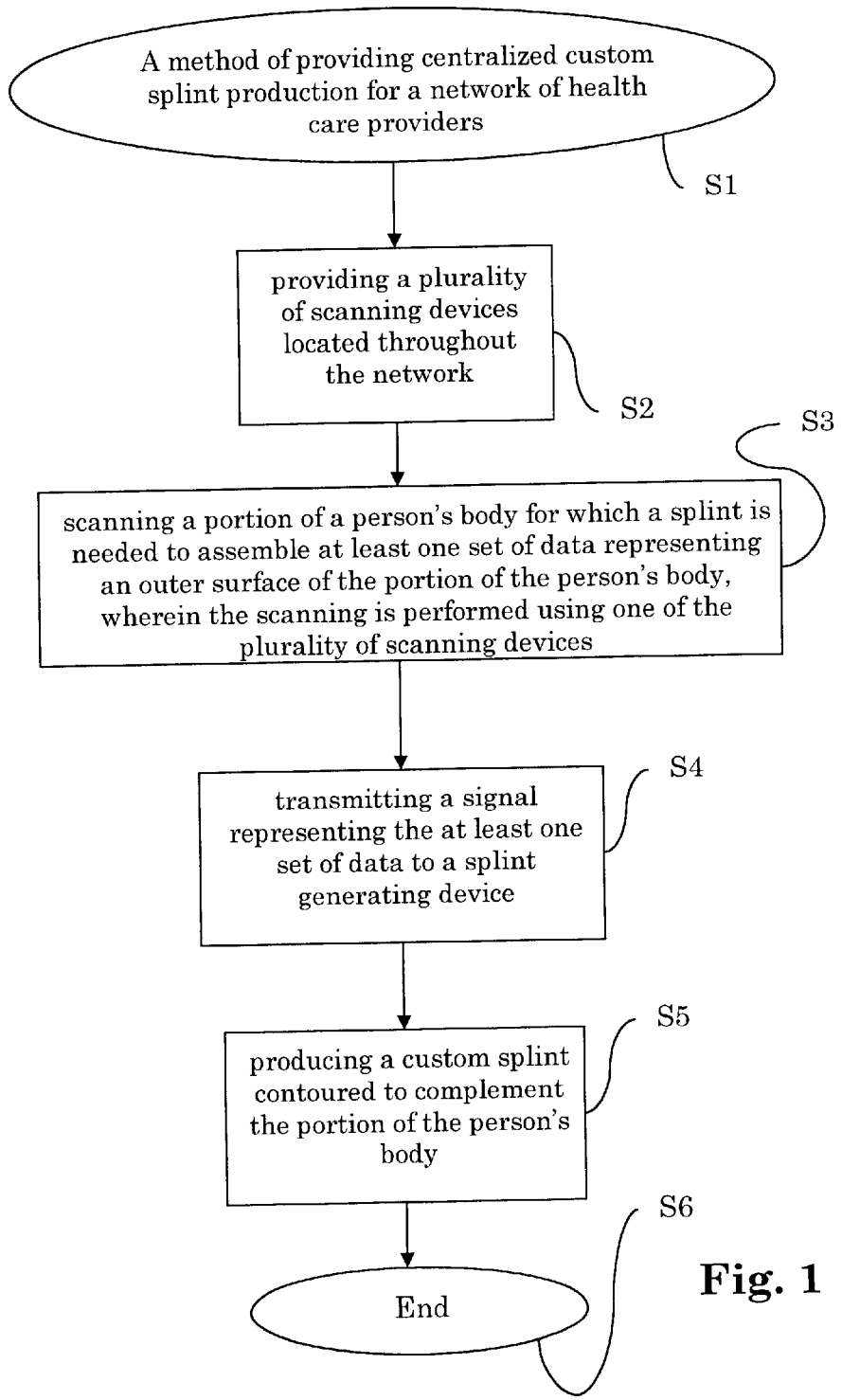
FIG. 1 is a flowchart of a preferred method of providing centralized custom splint production for a network of healthcare providers according to one embodiment of the present invention.
Figure 2:
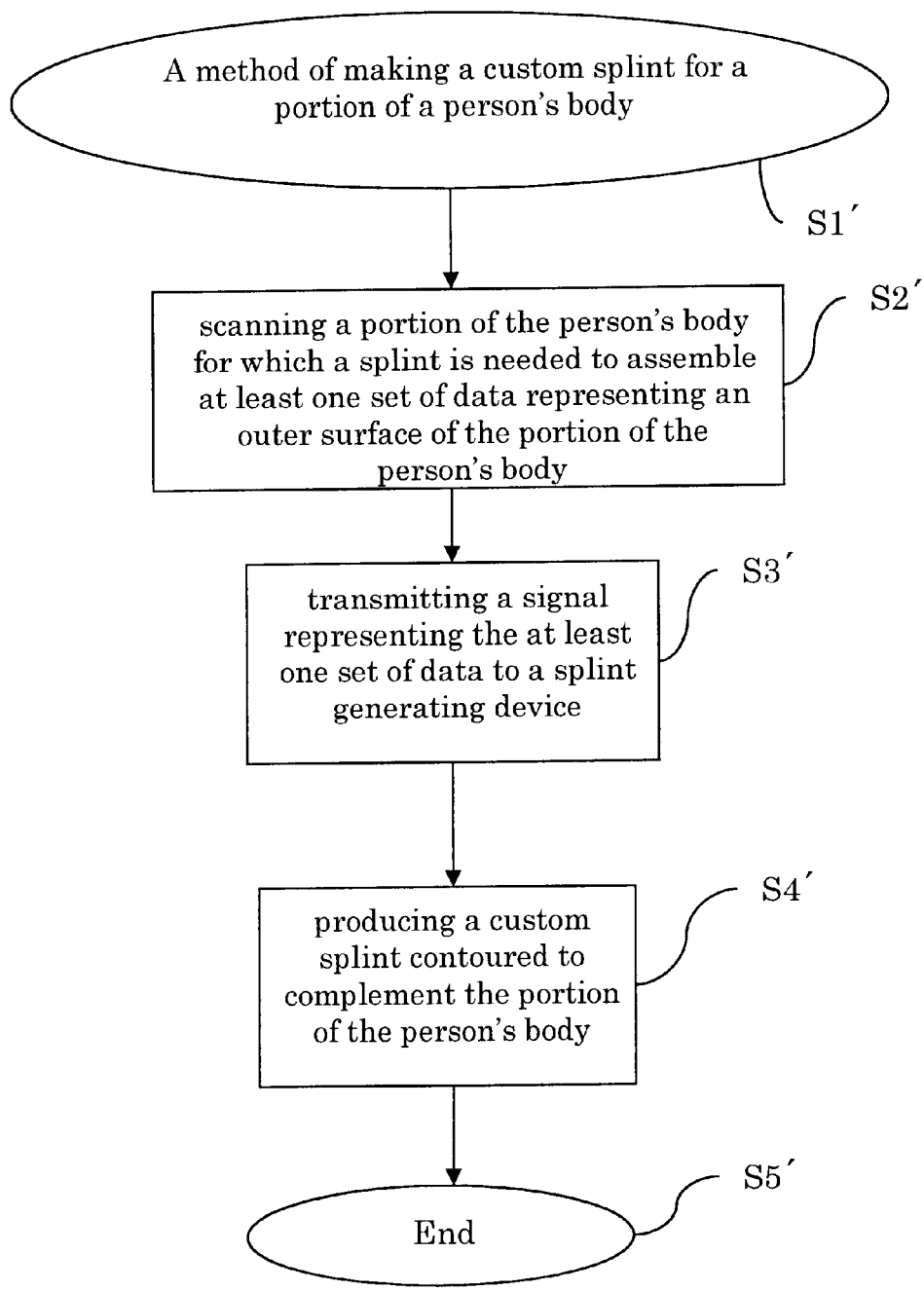
FIG. 2 is flowchart of a preferred method of making a custom splint for a portion of a person's body according to another embodiment of the present invention.

Referring to FIG. 1, a flowchart illustrating a preferred method of providing centralized custom splint production for a network of healthcare providers is illustrated. Referring to FIG. 2, a method of producing a custom splint for a portion of a person's body is illustrated.

The splint of the present invention is preferably made from a durable, high strength material, such as a suitable polymer. However, those of ordinary skill in the art will appreciate that any suitable splint material can be used without departing from the scope of the present invention.

Referring to FIGS. 1 and 2, the preferred methods of providing custom splints may include using a centralized custom splint producing device for one or more healthcare networks. The network that is serviced by the centralized custom generating device is preferably a network of healthcare providers that may be organized by region, hospital, and/or insurance carrier.

The preferred methods of the present invention preferably include the step of providing a plurality of scanning devices located throughout the network, preferably in individual offices or clinics. The scanning devices may be located within a regional hospital network to allow centralized production of custom splints or the scanning devices may be located within a regional healthcare practitioner network to allow centralized production of custom splints for the entire network. The scanning devices are preferably three dimensional image scanning devices capable of precisely measuring the outer contours of a portion of a person's body. The scanning devices can be designed so that one scanner can be used for any portion of a person's body, or the scanning devices can be customized for use with a person's leg, hand, wrist, and/or arm. The scanning devices can be used in conjunction with computer aided design software to define the appropriate shape of the custom splint.

The scanning devices may be connected to the splint generating device via the Internet, dial up modem connections, optical fiber connections, broadband connections, via cable, and/or any other known types of data transfer connectors. Alternatively, the data can be written onto a compact disc read only memory device or similar data storage device and transferred to the custom splint generating machine for processing and use thereafter without departing from the scope of the present invention.

The preferred methods of the present invention include scanning a portion of the person's body for which a splint is needed to assemble at least one set of data representing an outer surface of the portion of the person's body. The scanning is preferably performed using one of the scanning devices mentioned above. One example of a method of digitizing an outer surface of a portion of a person's body is disclosed in U.S. Pat. No. 5,432,703 which is entitled "laser digitizer system for producing orthodic and prosthetic devices", which is hereby incorporated by reference herein as if set forth in its entirety. Another example of collecting at least one set of data that represents a surface is disclosed in U.S. Pat. No. 5,768,134 which is entitled "Method for Making a Perfected Medical Model on the Basis of Digital Image Information of a Part of the Body", which is also hereby incorporated by reference herein in its entirety as if fully set forth.

The preferred methods of the present invention include transmitting a signal representing the at least one set of data to a splint generating device. As mentioned above, the transmitting of the signal can be accomplished by sending the signal via the Internet to a remotely splint generating device to facilitate centralized custom splint production for any of the networks discussed above.

The step of transmitting may include transmitting the signal to a Stereolithography machine. The use of stereolithography equipment allows for rapid prototyping of the desired custom splints. Stereolithography equipment constructs the custom splints directly from the at least one data set with little if any human intervention being required. Stereolithography may use an ultra violet laser to cure liquid resin, such as a photopolymer. As the ultra violet laser traces cross-sections of the desired custom splint, the photopolymer solidifies to create a custom splint, layer by layer. The at least one data set is preferably is formatted in the STL file format used by some stereolithographic machines. The in process custom splint is generally lowered as the next bottom most layer of the custom splint is completed. The curing process is repeated until the finished custom splint is prepared. If desired, the custom splint can be post processed to create a desired finish. To increase throughput, multiple splints can be prepared by the stereolithography machine at one time.

Alternatively, the signal can be transmitted to a custom splint generating device that incorporates computer numerical control equipment. Computer numerical equipment typically replaces one or more manufacturing processes by integrating multiple operator steps into a single machine. This allows for increased throughput relative to the individual construction of the custom splint. Computer numerical equipment will essentially carve the splint out of a block of material, such as polyethylene. To minimize waste, different size blanks, or templates, can be provided so that depending on the size of a particular custom splint, the nearest sized template can be selected.

Another method of making the custom splint is to use a model hand and/or arm (hereinafter referred to as "the model") that changes in size and shape depending on the measurements contained in the signal. This allows the model to be properly sized to have the splint formed or pressed on the model.

Alternatively, the signal can be transmitted to a custom splint generating device formed by a pin die manufacturing machine. A custom splint pin die manufacturing machine uses multiple pins that are controlled to vary the heights thereof. A polyurethane blanket or the like is placed over the pins to prevent them from forming dimples in the resulting custom splint and then the splint is molded thereon.

Another method of making custom splints is to position a moldable polymer on a malleable base, such as silica, sand, clay, or the like. A machine then presses the moldable polymer into the base while the machine uses a scanner to ensure that the polymer is suitably shaped. The machine can travel over the length of the polymer pressing down on the polymer in multiple locations until the entire polymer is properly shaped to provide the proper mold for the desired splint. Various post molding treatments are available to ensure that the polymer has the proper characteristics to serve as a mold. Alternatively, a laser can be used to cut a desired pattern on a disposable mold that is then used to prepare the needed splint.

The methods of the present invention include the step of producing the custom splint which is contoured to complement the portion of the person's body that was scanned by the scanning device. Those of ordinary skill in the art will appreciate from this disclosure that the custom splint can be produced for any portion of a person's body, such as arm, a leg, a hand, a wrist, or the like.

The methods of the present invention may include the step of sending the custom splint to a home or work address for the person for whom the custom splint is prepared. This allows for the quickest delivery of the custom splint to the end user. It is preferable that the methods of the present invention include the step of providing directions for the person for whom the custom splint is designed to enable that person to properly attach the custom splint without returning to a physician or hospital. Additionally, the methods of the present invention may include storing the custom splint data to allow easy construction of additional splints on an as needed basis for those prone to further injury, such as professional athletes.

It is recognized by those skilled in the art, that changes may be made to the above described embodiments without departing from the broad inventive concept thereof. It is understood, therefore, that this invention is not limited to the particular embodiments disclosed, but is intended to cover all modifications which are within the spirit and scope of the invention as defined by the appended claims and/or shown in the attached flowcharts.

What is claimed is:

1. A method of providing centralized custom splint production for a network of health care providers, comprising:
    providing a plurality of scanning devices located throughout the network;
    scanning a portion of a person's body for which a splint is needed to assemble at least one set of data representing an outer surface of the portion of the person's body, wherein the scanning is performed by placing the portion of the person's body directly into one of the plurality of scanning devices;
    transmitting a signal representing the at least one set of data to a splint generating device; and
    producing a custom splint directly from the at least one set of data, wherein the custom splint is contoured to complement and immobilize the portion of the person's body, the custom splint being generally rigid when worn by the person and not allowing motion between portions of the body onto which the splint is attached.

2. The method of claim 1, wherein the step of transmitting the signal further comprises transmitting the signal via the Internet to a remotely located splint generating device to facilitate centralized custom splint production.

3. The method of claim 1, further comprising the step of sending the custom splint to a home address for the person for whom the custom splint was prepared.

4. The method of claim 3, further comprising the step of providing directions for the person for whom the custom splint is designed to enable the person to properly attach the custom splint.

5. The method of 1, wherein the step of providing the plurality of scanning devices further comprises providing the plurality of scanning devices within a regional hospital network to allow centralized production of custom splints therefor.

6. The method of 1, wherein the step of providing a plurality of scanning devices further comprises providing the plurality of scanning devices within a regional health care practicioner network to allow centralized production of custom splints therefor.

7. The method of claim 1, wherein the step of producing the custom splint further comprises producing the custom splint for an arm.

8. The method of claim 1, wherein the step of producing the custom splint further comprises producing the custom splint for a leg.

9. The method of claim 1, wherein the step of producing the custom splint further comprises producing the custom splint for a hand.

10. The method of claim 1, wherein the step of producing the custom splint further comprises producing the custom splint for a wrist.

11. The method of claim 1, wherein the step of transmitting further comprises transmitting the signal to a Sterolithography machine.

12. The method of claim 1, wherein the step of transmitting further comprises transmitting the signal to a Computer Numerical Control machine.

13. The method of claim 1, wherein the slip of transmitting further comprises transmitting the signal to a pin die manufacturing machine.

14. A method of making a custom splint for a portion of a person's body, comprising:
    scanning a portion of the person's body for which a splint is needed to assemble at least one set of data representing an outer surface of the portion of the person's body, wherein the scanning is accomplished by placing the portion of the person's body directly into a scanning device;
    transmitting a signal representing the at least one set of data to a splint generating device;
    producing a custom splint directly from the at least one set of data, wherein the custom splint is contoured to complement and immobilize the portion of the person's body, the custom splint being generally rigid when worn by the person and not allowing for motion between portions of the body onto which the splint is attached.

15. The method of claim 14, wherein the step of transmitting the signal further comprises transmitting the signal to a remotely located splint generating device to allow for centralized custom splint production.

16. The method of claim 15, further comprising the step of sending the custom splint to a home address for the person for whom the custom splint was prepared.

17. The method of claim 16, further including the step of providing directions for the person for whom the custom splint is designed to enable the person to properly attach the custom splint.

18. The method of claim 14, further comprising the step of providing a plurality of scanning devices each capable of transmitting to the splint generating device.

19. The method of claim 14, wherein the step of producing the custom splint further comprises producing the custom splint for an arm.

20. The method of claim 14, wherein the step of producing the custom splint further comprises producing the custom splint for a leg.

21. The method of claim 14, wherein the step of producing the custom splint further comprises producing the custom splint for a hand.

22. The method of claim 14, wherein the step of producing the custom splint further comprises producing the custom splint for a wrist.

23. The method of claim 14, wherein the step of transmitting further comprises transmitting the signal to a Sterolithography machine.

24. The method of claim 14, wherein the step of transmitting further comprises transmitting the signal to a Computer Numerical Control machine.

25. The method of claim 14, wherein the step of transmitting further comprises transmitting the signal to a pin die manufacturing machine.

26. The method of claim 24, wherein the step of producing the custom splint includes selecting one of a plurality of differently sized blanks that is closest to a desired size of the custom splint for processing into the custom splint.

* * * * *